United States Patent
Seitz, III et al.

(10) Patent No.: US 12,414,832 B2
(45) Date of Patent: Sep. 16, 2025

(54) MULTIFUNCTIONAL ENCLOSURE FOR MEDICAL PROBES

(71) Applicant: John R. Seitz, IV, Oxford, PA (US)

(72) Inventors: John Russell Seitz, III; John R. Seitz, IV, Oxford, PA (US)

( * ) Notice: Subject to any disclaimer, the term of this patent is extended or adjusted under 35 U.S.C. 154(b) by 4 days.

(21) Appl. No.: 18/608,598

(22) Filed: Mar. 18, 2024

(65) Prior Publication Data
US 2024/0238060 A1    Jul. 18, 2024

Related U.S. Application Data

(63) Continuation-in-part of application No. 18/074,048, filed on Dec. 2, 2022, now Pat. No. 11,931,189, which is a continuation of application No. 17/479,559, filed on Sep. 20, 2021, now Pat. No. 11,517,387, which is a continuation of application No. 16/353,889, filed on Mar. 14, 2019, now Pat. No. 11,123,147, which is a continuation-in-part of application No. 14/936,336, filed on Nov. 9, 2015, now abandoned, which is a continuation of
(Continued)

(51) Int. Cl.
| | |
|---|---|
| A61B 50/20 | (2016.01) |
| A61B 1/00 | (2006.01) |
| A61B 1/12 | (2006.01) |
| A61B 50/22 | (2016.01) |
| A61B 50/30 | (2016.01) |
| A61M 25/00 | (2006.01) |
| A61B 90/70 | (2016.01) |

(52) U.S. Cl.
CPC .......... *A61B 50/20* (2016.02); *A61B 1/00137* (2013.01); *A61B 1/0014* (2013.01); *A61B 1/00144* (2013.01); *A61B 1/121* (2013.01); *A61B 50/22* (2016.02); *A61B 50/30* (2016.02); *A61M 25/002* (2013.01); *A61B 2050/314* (2016.02); *A61B 2090/701* (2016.02)

(58) Field of Classification Search
CPC ... A61B 50/20; A61B 1/00137; A61B 1/0014; A61B 1/00144; A61B 1/121; A61B 50/22; A61B 50/30; A61B 2050/314; A61B 2090/701; A61M 25/002
USPC ................................................. 206/363, 364
See application file for complete search history.

(56) References Cited

U.S. PATENT DOCUMENTS

| | | |
|---|---|---|
| 2,340,024 A | 1/1944 | Skaller |
| 3,203,545 A | 8/1965 | Grossman |
| 3,794,042 A | 2/1974 | De Klotz et al. |

(Continued)

FOREIGN PATENT DOCUMENTS

WO    WO 2008-119118 A1    10/2008

*Primary Examiner* — Jacob K Ackun
(74) *Attorney, Agent, or Firm* — Devlin Law Firm LLC

(57) ABSTRACT

A multifunctional enclosure is described having an elongated sleeve configured with an enlarged opening for the insertion of an elongated member of a medical probe. The multifunctional enclosure is configured to prevent the elongated member of the medical probe from swinging and becoming damaged during transport. The multifunctional enclosure may further comprise an attachment component for securing the medical probe to the multifunctional enclosure. Furthermore, at least one vent may be configured onto the multifunctional enclosure, such as on a first end closure portion. The vent may allow for adequate flow for sterilization and/or drying.

18 Claims, 12 Drawing Sheets

Related U.S. Application Data application No. 13/235,522, filed on Sep. 19, 2011, now Pat. No. 9,277,966.

(60) Provisional application No. 61/386,035, filed on Sep. 24, 2010.

(56) References Cited

U.S. PATENT DOCUMENTS

| | | | |
|---|---|---|---|
| 3,861,395 A | 1/1975 | Taniguchi | |
| 3,956,011 A | 5/1976 | Carleton | |
| 4,754,877 A | 7/1988 | Johansson et al. | |
| 4,772,275 A | 9/1988 | Erlich | |
| 4,815,470 A | 3/1989 | Curtis et al. | |
| 4,823,949 A | 4/1989 | Bala | |
| 4,878,762 A | 11/1989 | Uddo Jr et al. | |
| 4,898,586 A | 2/1990 | McDonough | |
| 4,928,917 A | 5/1990 | Wolf | |
| 4,997,084 A | 3/1991 | Opie et al. | |
| 5,125,416 A | 6/1992 | Phillips | |
| 5,217,114 A | 6/1993 | Gadberry et al. | |
| 5,340,550 A | 8/1994 | Johnsen et al. | |
| 5,415,287 A | 5/1995 | Hamano et al. | |
| 5,514,074 A | 5/1996 | Yabe et al. | |
| 6,361,751 B1 | 3/2002 | Hight, III | |
| 6,375,006 B1 | 4/2002 | Samuels | |
| 6,793,882 B1 | 9/2004 | Verschuur | |
| 6,994,823 B2 | 2/2006 | Hight, III | |
| 7,290,926 B2 | 11/2007 | Yu | |
| 7,845,850 B2 | 12/2010 | Hsieh | |
| 7,874,426 B2 | 1/2011 | Castellani | |
| 8,579,115 B2 | 11/2013 | Murphy et al. | |
| 9,277,966 B2 * | 3/2016 | Seitz, III | A61M 25/002 |
| 11,123,147 B2 * | 9/2021 | Seitz, III | A61B 1/0014 |
| 11,517,387 B2 * | 12/2022 | Seitz, III | A61B 1/0014 |
| 11,931,139 B2 | 3/2024 | Seitz, III | |
| 11,931,189 B2 * | 3/2024 | Seitz, III | A61B 1/00137 |
| 2002/0068028 A1 | 6/2002 | Hight, III | |
| 2002/0117412 A1 | 8/2002 | Rabiner et al. | |
| 2003/0192799 A1 | 10/2003 | Addy et al. | |
| 2004/0245136 A1 | 12/2004 | Nordquist | |
| 2004/0256264 A1 | 12/2004 | Israelsson et al. | |
| 2005/0103663 A1 | 5/2005 | Jolley et al. | |
| 2006/0116551 A1 | 6/2006 | Lovett et al. | |
| 2006/0278546 A1 | 12/2006 | State et al. | |
| 2007/0009376 A1 | 1/2007 | Hamada et al. | |
| 2008/0251102 A1 | 10/2008 | Haack et al. | |
| 2008/0271270 A1 | 11/2008 | Sawada et al. | |
| 2008/0319423 A1 | 12/2008 | Tanghoj et al. | |
| 2009/0000970 A1 | 1/2009 | Bordeau et al. | |
| 2009/0008279 A1 | 1/2009 | Tanghoej | |
| 2009/0112063 A1 | 4/2009 | Bakos et al. | |
| 2009/0166306 A1 | 7/2009 | Ahearn | |
| 2009/0200187 A1 | 8/2009 | Nestenborg et al. | |
| 2010/0042045 A1 | 2/2010 | Splvey | |
| 2010/0087801 A1 | 4/2010 | Torstensen et al. | |
| 2011/0137428 A1 | 6/2011 | Terliuc | |
| 2015/0090620 A1 | 4/2015 | Seitz, III | |

\* cited by examiner

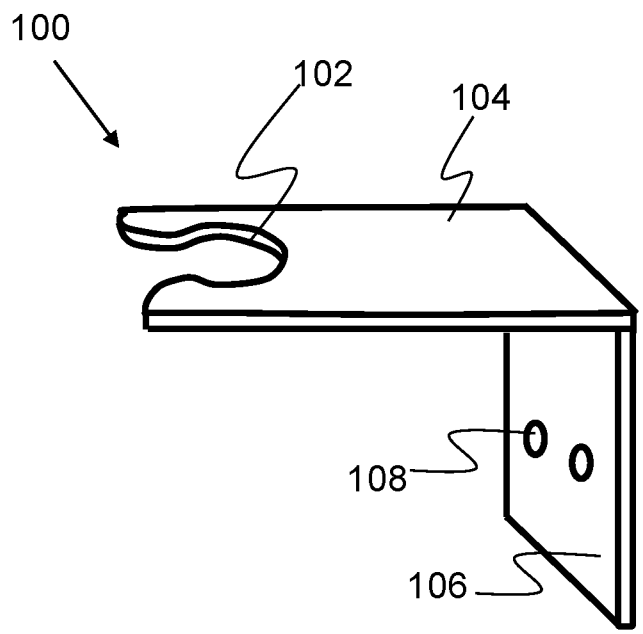
FIG. 8A
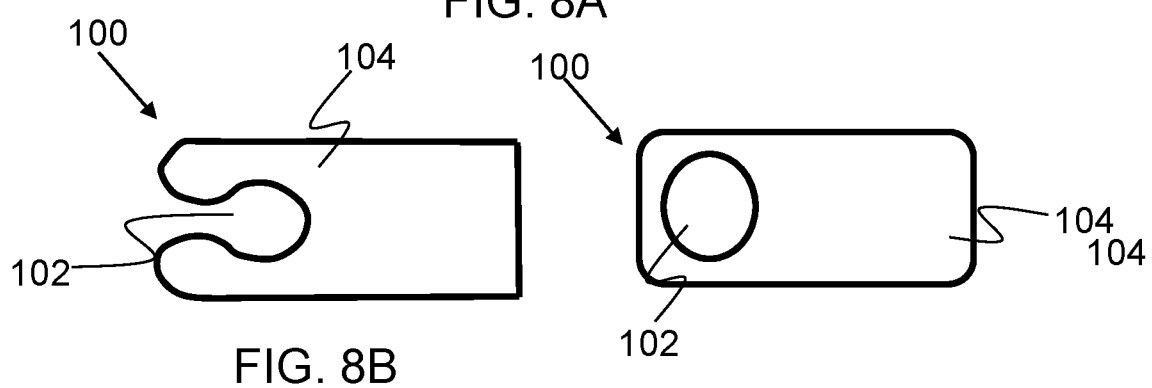
FIG. 8B
FIG. 8C
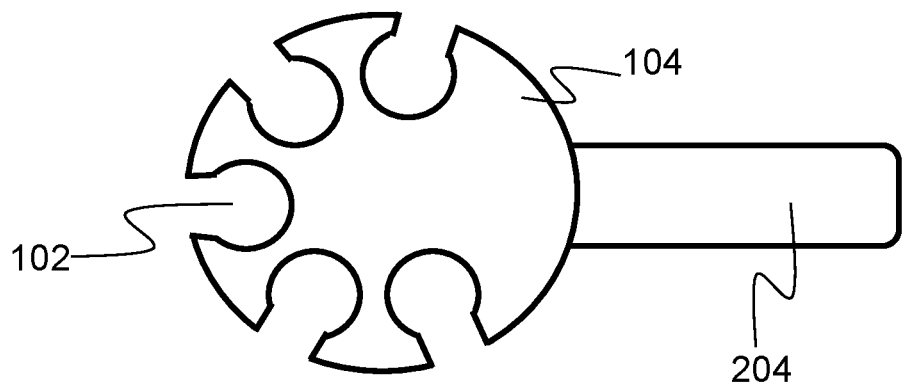
FIG. 8D

MULTIFUNCTIONAL ENCLOSURE FOR MEDICAL PROBES

CROSS-REFERENCE TO RELATED APPLICATIONS

This application is a continuation in part of U.S. patent application Ser. No. 18/074,048, filed Dec. 2, 2022, and currently, which is a continuation of U.S. patent application Ser. No. 17/479,559, filed Sep. 20, 2021, now issued as U.S. Pat. No. 11,517,387, which is a continuation of U.S. patent application Ser. No. 16/353,889, filed Mar. 14, 2019, now issued as U.S. Pat. No. 11,123,147, which is a continuation in part of U.S. patent application Ser. No. 14/936,336, filed Nov. 9, 2015, now abandoned, which is a continuation of U.S. patent application Ser. No. 13/235,522, filed Sep. 19, 2011, and now issued as U.S. Pat. No. 9,277,966, which claims the benefit of priority to U.S. Provisional Patent Application No. 61/386,035, filed Sep. 24, 2010, the disclosures of which are incorporated herein in their entirety.

BACKGROUND OF THE INVENTION

Field of the Invention

The invention relates to multifunctional enclosures for medical probes including endoscopes or instruments and methods of using the enclosure including but not limited to: protecting the medical probe during transport, storing and cleaning the medical probe, enclosing and protecting the medical probe during sterilization, and providing a post procedural reservoir for cleaning and/or sterilizing fluid.

Background

Medical probes are routinely used for various medical procedures whereby they are inserted into the body and in many cases are equipped with a means to view inside the body. Medical probes are expensive instruments that typically comprise an elongated portion that is inserted into the body. These elongated members or elongated portions are usually designed to be flexible to allow for maneuvering and locating the tip at a desired location in the body. The flexibility and length of the elongated portion of the medical probe make them difficult to handle. The elongated portions of the medical probe may unintentionally swing and hit object during handling or transport and become damaged or contaminated. Medical probes must be sterilized or disinfected after each use, which requires a considerable amount of handling including transport to a cleaning facility, transport to and handling during sterilization/disinfection, transport to and handling during storage, and finally transport to and handling during medical procedures. After a medical procedure is complete, the contaminated medical probe may pose a contamination risk to the operating room, or other medical room. Body fluids and other body contaminates may drip or fling off of the elongated portion of the medical probe, and create a cross contamination risk.

During sterilization/disinfection procedures, the medical probe, or in some cases the elongated member of the medical probe, may be placed into a sterilization/disinfection chamber, such as, steam, ethylene oxide, ozone or the like. Handling of the medical probe during these repetitive procedures introduces possible cross contamination by placing the device directly on surfaces where other devices have previously been located. In addition, these repetitive procedures subject the medical probe to damage, along the length, and especially to the highly sensitive tip of the medical probe.

There exists a need for a multifunctional enclosure for medical probes that can be used to protect the elongated member or portion of the medical probe during transport, storage, cleaning, sterilization, and provide a post procedural reservoir for cleaning and/or sterilizing fluid.

SUMMARY OF THE INVENTION

The invention is directed to a multifunctional enclosure for medical probes and in particular the elongated members or portions of an endoscopic device. The multifunctional enclosure comprises an elongated sleeve having a first end, a second end and an attachment component. The first end may be closed and the elongated member of the medical probe may be inserted through the second end. The elongated sleeve may be rigid in order to prevent the elongated member of the medical probe from swinging or moving during transport or handling. In one embodiment, the elongated sleeve is a tube, and may be a plastic tube. The elongated sleeve may be configured in a generally straight shape, or comprise at least one bend or curve. In addition, the elongated sleeve as described herein, may be a "U" shape, or configured in a helical shape, wherein at least a portion of the elongated sleeve is in a helical configuration. The elongated sleeve may have an aspect ratio of greater than about 3, or more.

The first end of the multifunctional enclosure may be closed or may comprise a detachable first end cover portion, such as a cap or plug. The first end cover portion may be removed during cleaning or sterilization procedures to allow for flow through the elongated sleeve. In addition, the first end cover portion may be removed to allow for adequate drying after cleaning or sterilization. In one embodiment the first end, or first end cover portion comprises a vent. A vent may be configured anywhere on the multifunctional enclosure, and the vent may be an antimicrobial, and/or hydrophobic. In yet another embodiment the first end cover portion comprises a seam where the first end of the multifunctional enclosure has been sealed. For example, the first end of a plastic multifunctional enclosure may be heat pressed and welded together for form a seal. In still another embodiment, the first end of the multifunctional enclosure may be molded in such a way to form a cover over the end of the elongated member of the multifunctional enclosure.

A pouch, cap or plug may be attached or sealed over the first end or second end to protect interior of the multifunctional enclosure from contaminates prior to use. The pouch, cap or plug may be removed prior to use and a clean first end cover portion may be used attached to the first end.

The second end of the multifunctional enclosure may comprise an enlarged end or opening configured to facilitate the insertion of the medical probe. The second end may be a funnel shape or an irregular shape. In one embodiment, the second end comprises a cover that may be removed to allow for the insertion of the medical probe. In an alternative embodiment, the second end cover may comprise an opening, such as a hole or at least one slit, whereby the medical probe may be inserted. The second end cover may protect the interior of the multifunctional enclosure from contamination prior to use. In one embodiment the multifunctional enclosure, comprises two second end covers; one being solid, and the other having an opening. In this embodiment, the solid second end cover may be removed and the medical probe may be inserted through the opening in the other second end cover. The second end may further comprise at least one flute whereby the air may pass when a medical probe is inserted into the multifunctional enclosure. The flute or flutes may comprise channels along at least a portion of the length of the enlarged end. In one embodiment, the second end comprises a plurality of flutes extending the length of the enlarged end.

The attachment component may comprise any number of components configured to attach the multifunctional enclosure to the medical probe. The attachment component may include for example, elastic bands, hooks, latches, hook and loop fasteners and the like. In one embodiment, the attachment component comprises at least one elastic band that may be detachably attached to the medical probe, such as by stretching the band and locating the stretched end over a portion of the medical probe.

The multifunctional enclosure may further comprise an enclosure pouch that may be configured to enclose the end of the medical probe that extends from the multifunctional enclosure. In one embodiment, the enclosure pouch is attached to the multifunctional enclosure, and comprises a sealing portion along the extended end that may be used to seal the medical probe within the enclosure pouch.

The multifunctional enclosure system may further include a probe retainer that is configured between the elongated portion of the medical probe and the interior or interior wall of the elongated rigid sleeve. A probe retainer is configured to extend around the elongated portion of the medical device of the medical probe. A medical device on the extended end of the elongated portion may be fragile and preventing it from jostling within the elongated sleeve may be important to prevent damage to the medical device. An exemplary probe retainer fits within the elongated sleeve and has an aperture extending from a proximal opening. The aperture may be a through aperture and extend from the proximal opening to a distal opening. The probe retainer may form a ring around the elongated portion of the medical probe. The proximal opening may be larger in dimension or diameter than the distal opening and may be configured proximal to the second end or the opening of the elongated member for insertion of the elongated portion. The aperture may be tapered from the proximal opening to the distal end of the probe retainer or to the distal end opening. This tapering may allow easier insertion of the extended end of the elongated portion of the medical probe. The probe retainer may be configured within the elongated member and may be configured to slide with the elongated member down toward the first end upon insertion of the elongated portion of the medical probe. In this way, medical probes with various length elongated members may have the medical device on the extended end protected as the probe retainer slides down with the elongated member to be positioned proximal to the medical device or extended end of the elongated portion of the medical probe. The distal opening may be smaller than a diameter of the elongated portion.

An exemplary probe retainer is elastic, wherein it can be deformed by a deforming force and then return to an original shape upon removal of the deforming force, such as a foam or elastomeric material. A preferred probe retainer comprises foam as it is easily deformable and will provide effective cushioning and retention of the elongated portion of the medical probe.

A probe retainer may be configured within the elongated sleeve of may be provided separately, such as within a pouch configured over the second end opening of the elongated sleeve. A user may remove the probe retainer and slid in into the elongated sleeve prior to insertion of the elongated portion of the medical probe. The probe retainer may then receive the extended end of the elongated portion of the medical probe and slide down along the elongated sleeve with the elongated portion of the medical probe. A user may also remove the probe retainer from the pouch and may configure the probe retainer on or around the elongated portion of the medical probe prior to insertion of the medical probe into the elongated sleeve. Also, the probe retainer may be configured more proximal to the first end of the elongated sleeve, such a proximal to the first end closure and may be configured to receive and retain the elongated portion of the medical probe therein.

The multifunctional enclosure as described herein may be used in a variety of ways. In one method of use, a medical probe or the elongated portion of a medical probe may be inserted into the multifunctional enclosure as described herein, and the medical probe may be securely transported to and/or from, a medical procedural room, storage area, cleaning facility, or a sterilization procedure. In another embodiment, the multifunctional enclosure may be used as a reservoir for fluids that may coated onto the medical probe prior or after a procedure. For example, the medical probe may be coated with a sterilization fluid prior to a procedure by introducing the fluid into the multifunctional enclosure. The medical probe may then be removed from the multifunctional enclosure and inserted into a patient. In addition, the medical probe may be coated or treated with a cleaning solution or sterilization fluid after a procedure. For example, a cleaning fluid, such as enzyme soap, for example, may be introduced into the multifunctional enclosure, and the medical probe may be inserted into the multifunctional enclosure for post procedural cleaning. Quickly treating the medical probe with a cleaning or sterilization fluid after a procedure may reduce the risk of cross contamination occurring and may provide for more effective and complete removal of biological material.

The summary of the invention is provided as a general introduction to some of the embodiments of the invention, and is not intended to be limiting. Additional example embodiments including variations and alternative configurations of the invention are provided herein.

BRIEF DESCRIPTION OF THE DRAWINGS

The accompanying drawings are included to provide a further understanding of the invention and are incorporated in and constitute a part of this specification, illustrate embodiments of the invention, and together with the description serve to explain the principles of the invention.

FIG. 8A shows an isometric view of a bracket described herein.

FIGS. 8B and 8C show top views of brackets described herein.

FIG. 8D shows a retainer for a plurality of multifunctional enclosures.

Reference numbers to elements are used consistently throughout the figures; however, the elements may have different embodiments such as shape, or configuration, for example.

DETAILED DESCRIPTION OF THE ILLUSTRATED EMBODIMENTS

Figure 1:
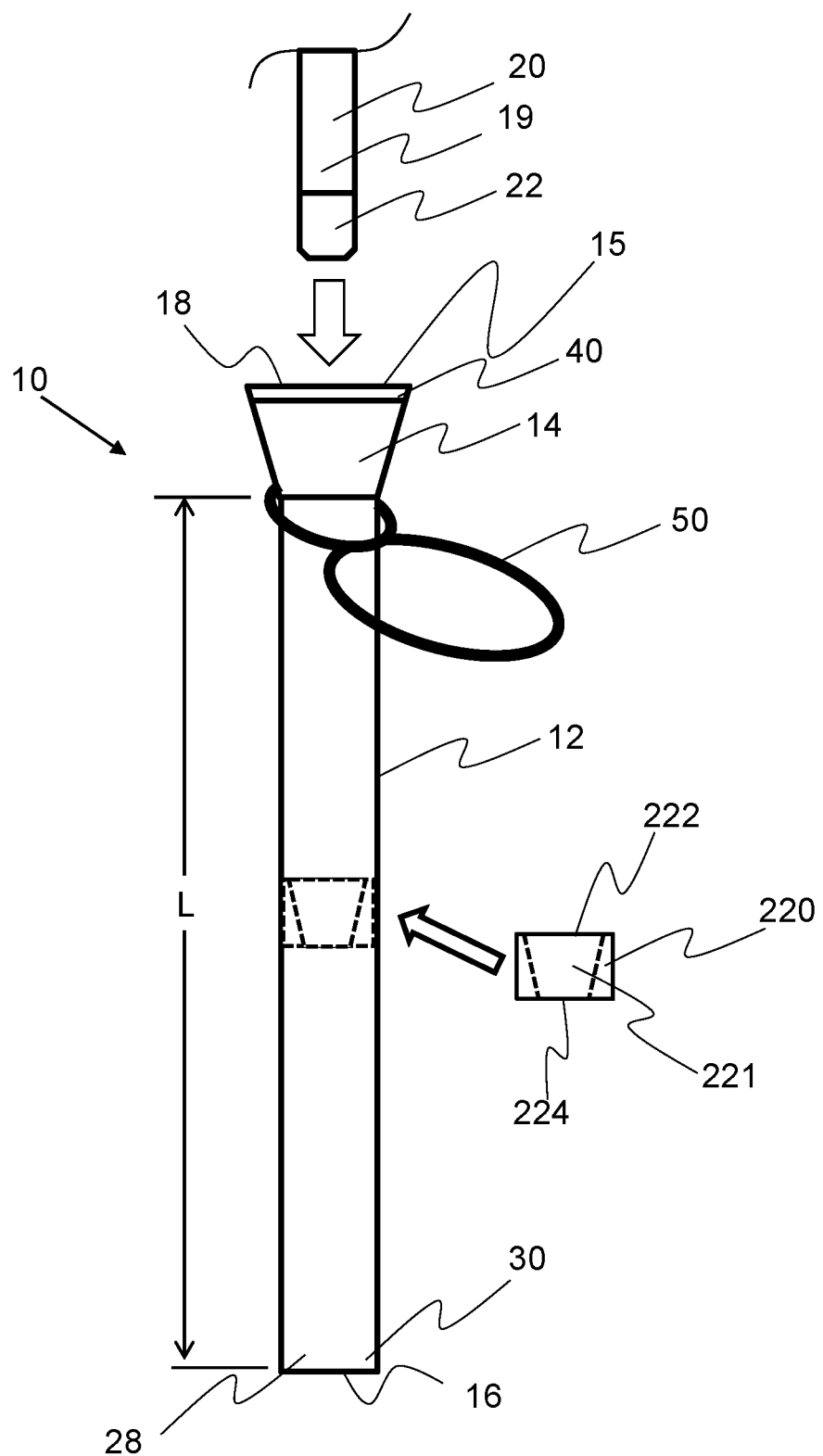
FIG. 1 shows a side view of a multifunctional enclosure described herein.

The invention is directed to a multifunctional enclosure for medical probes and in particular the elongated portions of a medical probe. As shown in FIG. 1, the multifunctional enclosure 10 comprises an elongated sleeve 12 having a first end 16, a second end 18 and an attachment component 50. In this embodiment, the first end comprises a first end closure portion 30, and the elongated member or elongated portion 19 of the medical probe 20 may be inserted through the second end. A medical probe may have a medical device 22 on an elongated end of the elongated portion 19, as shown in FIG. 1. The elongated sleeve 12 may be rigid as defined herein, in order to prevent the elongated portion of the medical probe from swinging or moving during transport or handling. The elongated sleeve may be made out of any suitable material including but not limited to plastic, metal, glass, composites, combinations of said materials, and the like. The elongated sleeve may be made out of a material that is capable of being sterilized with ozone, ethylene oxide, and/or steam sterilization multiple times without degradation. Polysulfone, Ultem®, PPSU, and PEEK can be used for medical devices where repeated steam sterilization is required. Plastics that are well suited for ozone sterilization include, but are not limited to, polyvinylidene fluoride (PVDF), Polyvinyl Chloride (PVC), polyurethane, polypropylene, polyethylene, polyetherether ketone (PEEK), polycarbonate, Kalrez, and Acrylonitrile Butadiene Styrene (ABS). Many plastics are well suited for ethylene oxide sterilization as this gas is less corrosive than ozone and the temperature of sterilization may be less than steam sterilization.

The elongated sleeve may be transparent or translucent, opaque or a specific color to indicate a particular type of multifunctional enclosure. In some embodiments, the multifunctional enclosure, or the elongated sleeve of the multifunctional enclosure may be transparent to allow for easy recognition of the medical probe inside. In addition, a transparent or translucent multifunctional enclosure, may allow a user to determine the level of cleaning or other fluid introduced into the multifunctional enclosure.

Figure 6A:
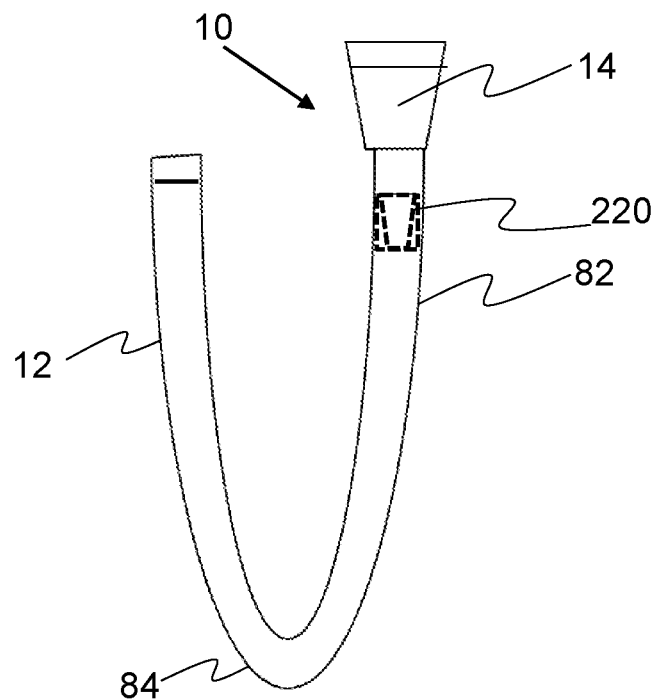
FIG. 6A shows a side view of a multifunctional enclosure described herein having a "U" shaped elongated sleeve.
Figure 6B:
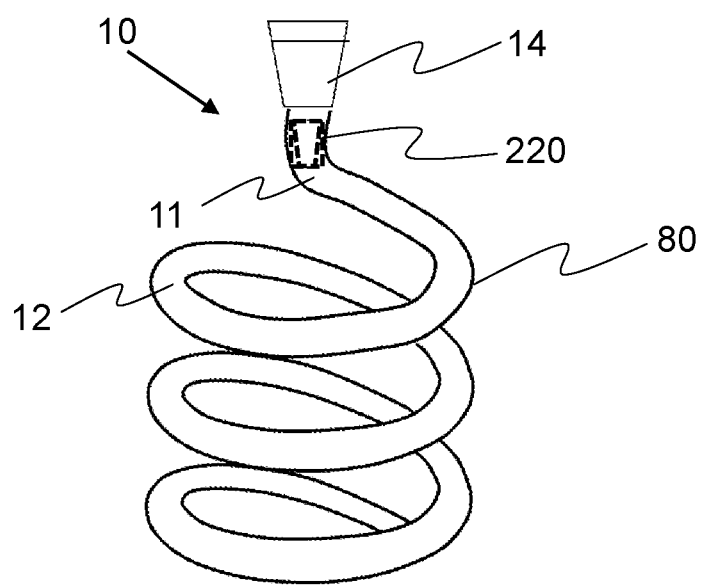
FIG. 6B shows a side view of a multifunctional enclosure described herein having a helically shaped elongated sleeve.

In one embodiment, the elongated sleeve is a tube, such as a plastic tube. The elongated sleeve may be configured in a generally straight shape, or comprise at least one bend or curve. In addition, the elongated sleeve as described herein may be a "U" shape 82 as shown in FIG. 6A having a bend 84. In another embodiment, the elongated sleeve, or a portion of the elongated sleeve 12 may be configured into helical shape. The helical elongated sleeve 80, may comprise one or more generally straight sections as shown in FIG. 6B.

Figure 5A:
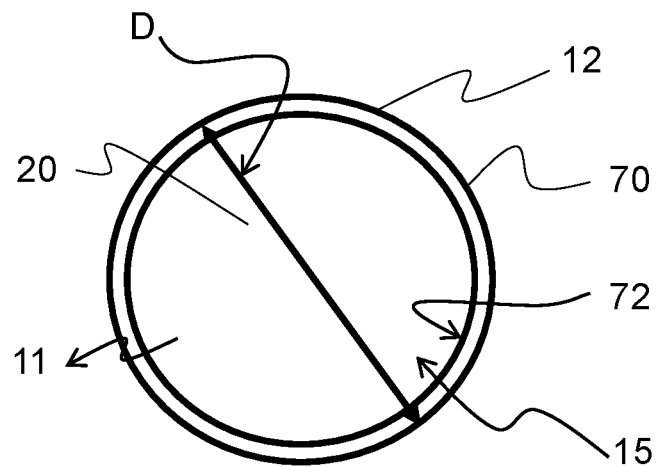
FIG. 5A show a cross sectional view of the elongated sleeve described herein.
Figure 5B:
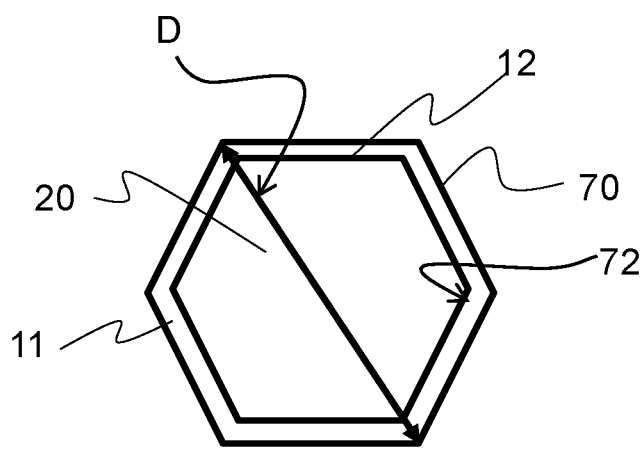
FIG. 5B show a cross sectional views of the elongated sleeve described herein.

The elongated sleeve may have an aspect ratio of length L over maximum outer dimension, or outer diameter D, as shown in FIG. 1, greater than about 3, or more. The maximum outer dimension D is the maximum dimension that can be measured across the cross section of the elongated member as shown for example in FIGS. 5A and 5B. When the elongated member is a tube with opening 15, the maximum outer dimension is simply the outer diameter of the tube as shown in FIG. 5A. When the elongated member is a polygonal or irregular shape it is the maximum dimension measured as shown in FIG. 5B. The aspect ratio of the elongated sleeve may be any suitable value such as but not limited to greater than about 5, greater than about 8, or greater than about 10, to accommodate various types of medical probe.

The length of the elongated member of the multifunctional enclosure can be any suitable length to accommodate the medical probe and may be, for example, greater than about 6 in, greater than about 12 in, greater than about 20 in, greater than about 40 in, greater than about 60 in, greater than about 80 in, or any range between lengths described including, for example, from about 6 in to 80 in, or 6 in to 60 in.

The diameter or maximum outer dimension of the elongated member of the multifunctional enclosure may be any suitable dimension to accommodate the medical probe and may be, for example, greater than about 0.1875 in, greater than about 0.25 in, greater than about 0.5 in, greater than about 1.0 in, greater than about 1.25 in, greater than about 1.5 in, greater than about 2.0 in, or any range between lengths described including, for example, from about 0.1875 in to 2.0 in, or 0.25 in to 1.5 in.

The elongated sleeve of the multifunctional enclosure may have any suitable cross sectional shape, such as a circular shape as shown in FIG. 5A, or a polygon shape, as depicted in FIG. 5B as a hexagonal shape. Any suitable shape may be used, and in some embodiments, an irregular or polygonal shape may be used to avoid creating a seal against the medical probe at the second end. The elongated sleeve 12 is configured such that the medical probe 20 may easily slide in and out of the elongated sleeve 12 as shown in FIG. 1. The medical probe may be positioned within the elongated sleeve through the opening 15 with a sufficient clearance from the inside surface 72.

Figure 2A:
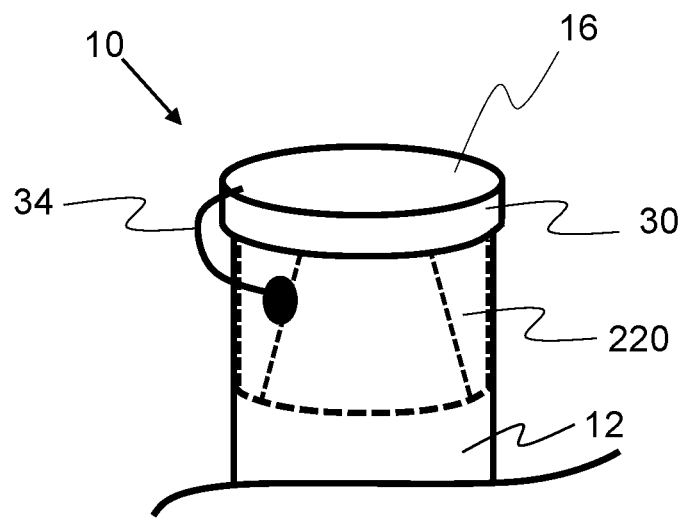
FIG. 2A shows an isometric view of the first end of a multifunctional enclosure described herein.

The first end 16 of the multifunctional enclosure 10 may comprise a first end closure portion 30, such as a detachable cap 28, as shown in FIG. 1. The first end closure portion may be removed during cleaning or sterilization procedures to allow for flow through the elongated sleeve. In addition, the first end closure portion may be removed to allow for adequate drying after cleaning or sterilization. A first end closure attachment portion 34, as shown in FIG. 2A, may allow the first end cover to be removed from the end without being completely removed from the multifunctional enclosure. The first end closure attachment portion may comprise any suitable means to attach the first end closure portion 30 to the multifunctional enclosure 10. As shown in FIG. 2A, the first end closure attachment portion 34 comprises a piece of material attached to the first end cover at one end and attached to the elongated member at the opposing end.

The first end closure portion may be a cap that extends over the outer surface of the elongated member, or may be a plug that comprises a portion that is inserted into the opening of the first end. The first end closure portion may be configured to be detachably attached to the first end and may comprise threads such that the first end portion may be screwed onto the first end. Threads may be configured onto the inside and/or outside surface of either the first end closure portion or the first end. In another embodiment, the first end closure portion may be pushed onto the first end and may be designed with tolerances to adequately seal the first end. In addition, the first end closure portion may be snapped onto the first end, and either the closure portion or the first end may comprise at least one raised element, or ridge, that provides an interference fit for the closure portion to be snapped on. In yet another embodiment, the first end closure portion may expand or contract to seal the first end. The first end closure portion may comprise an elastomer to secure the closure portion to the first end.

Figure 2B:
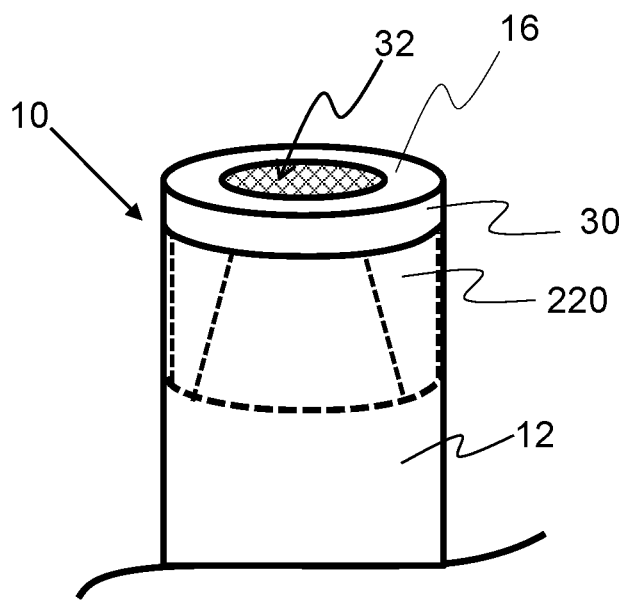
FIG. 2B shows an isometric view of the first end of a multifunctional enclosure described herein having a vent.
Figure 2C:
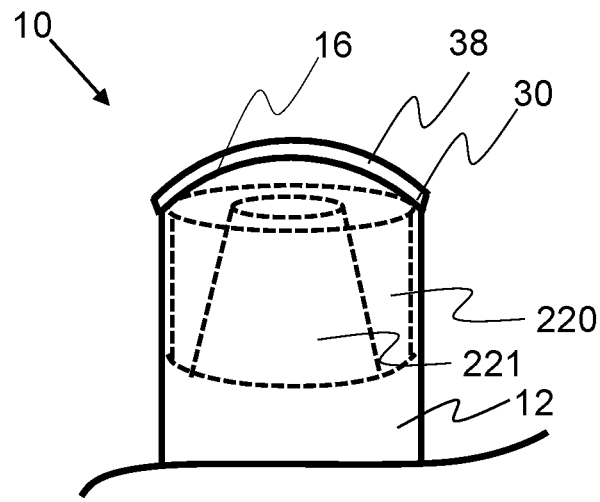
FIG. 2C shows a side view of the first end of a multifunctional enclosure described herein having a seam.
Figure 2D:
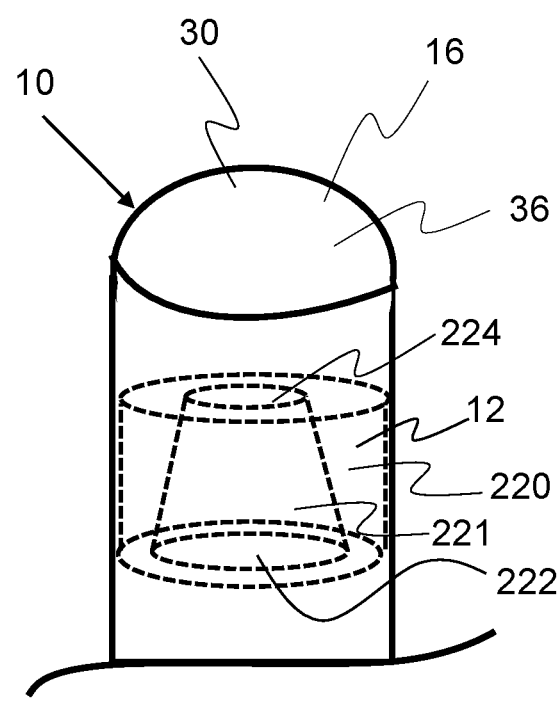
FIG. 2D shows an isometric view of the first end of a multifunctional enclosure described herein having molded end.

In yet another embodiment, the first end closure portion comprises a seam 38 where the first end 16 of the multifunctional enclosure 10 has been sealed as shown in FIG. 2C. For example, the first end of a plastic multifunctional enclosure may be heat pressed and welded together to form a seal and first end closure portion. In still another embodiment, the first end 16 of the multifunctional enclosure 10 may comprise a molded end 36, as shown in FIG. 2D. The molded end may be configured in any suitable shape, such as a rounded or spherical shape.

Figure 4:
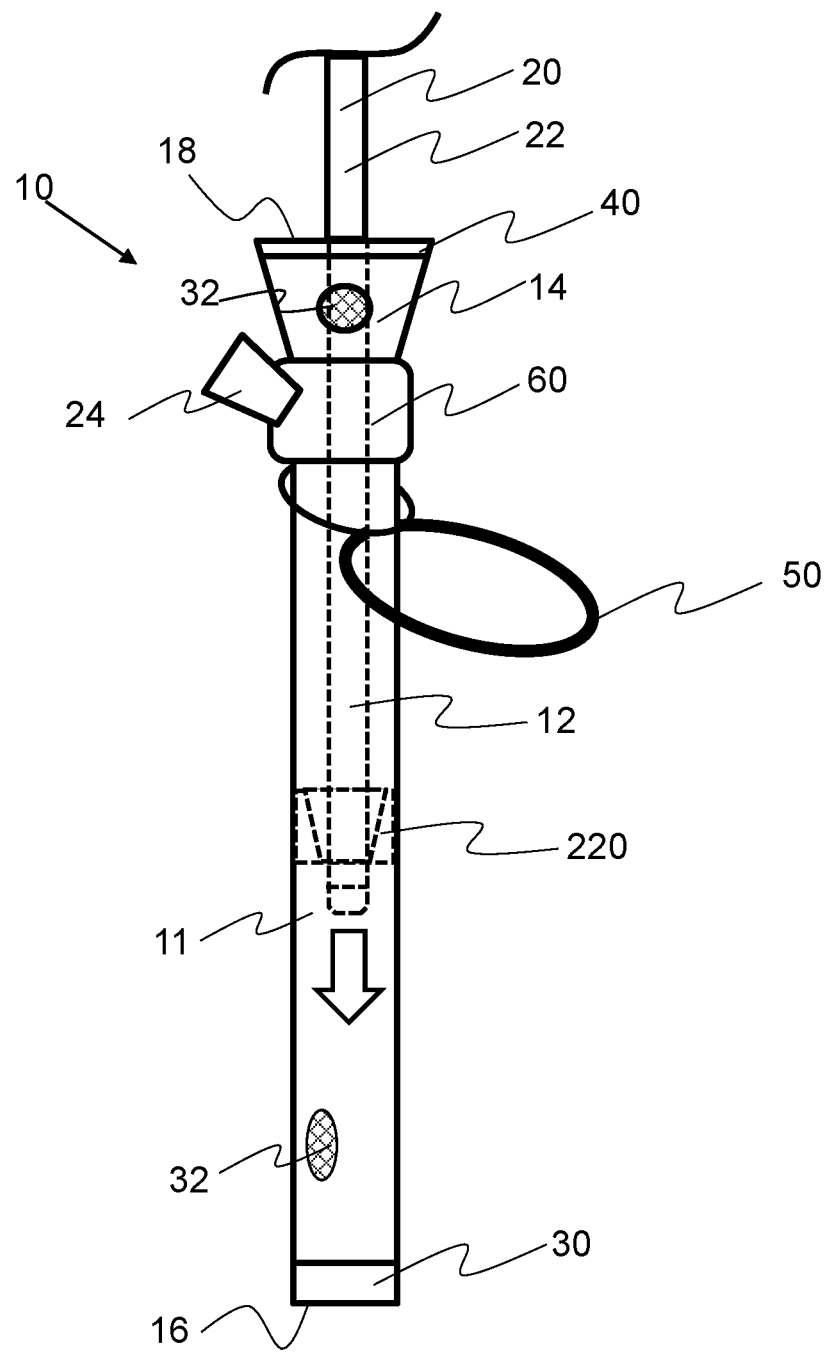
FIG. 4 shows a side view of a multifunctional enclosure described herein having an attachment component and two vents.

In one embodiment, the first end, or first end cover 30 comprises a vent 32 as shown in FIG. 2B. A vent, however, may be configured anywhere on the multifunctional enclosure 10 as shown in FIG. 4. The vent may be antimicrobial, and/or hydrophobic. In one embodiment, the vent comprises a porous material that meets standards for antibacterial ratings, such as materials having a log reduction value (LRV) of more than 99.999 when tested according to ASTM F1608. The vent may have sufficient air flow to allow for adequate drying of the medical probe after cleaning, sterilization, or during storage. The vent may comprise a material that has a gurley value as measured with a Gurley Densometer 4380, of no more than 100 seconds, and may have gurley values of no more than about 5 seconds, no more than about 20 seconds, no more than about 50 seconds. The vent material may comprise expanded polymers such as expanded polytetrafluoroethylene membrane, microfiber materials, sintered polymers such as Zitex membranes available from Saint Gobain Inc., Worchester, Mass., SureVent membranes available from Millipore Inc., Bellercia, Mass., and the like. The hydrophobic vent may allow fluid to be poured into the enclosure while also allowing for adequate air flow during sterilization and/or drying.

Figure 3A:
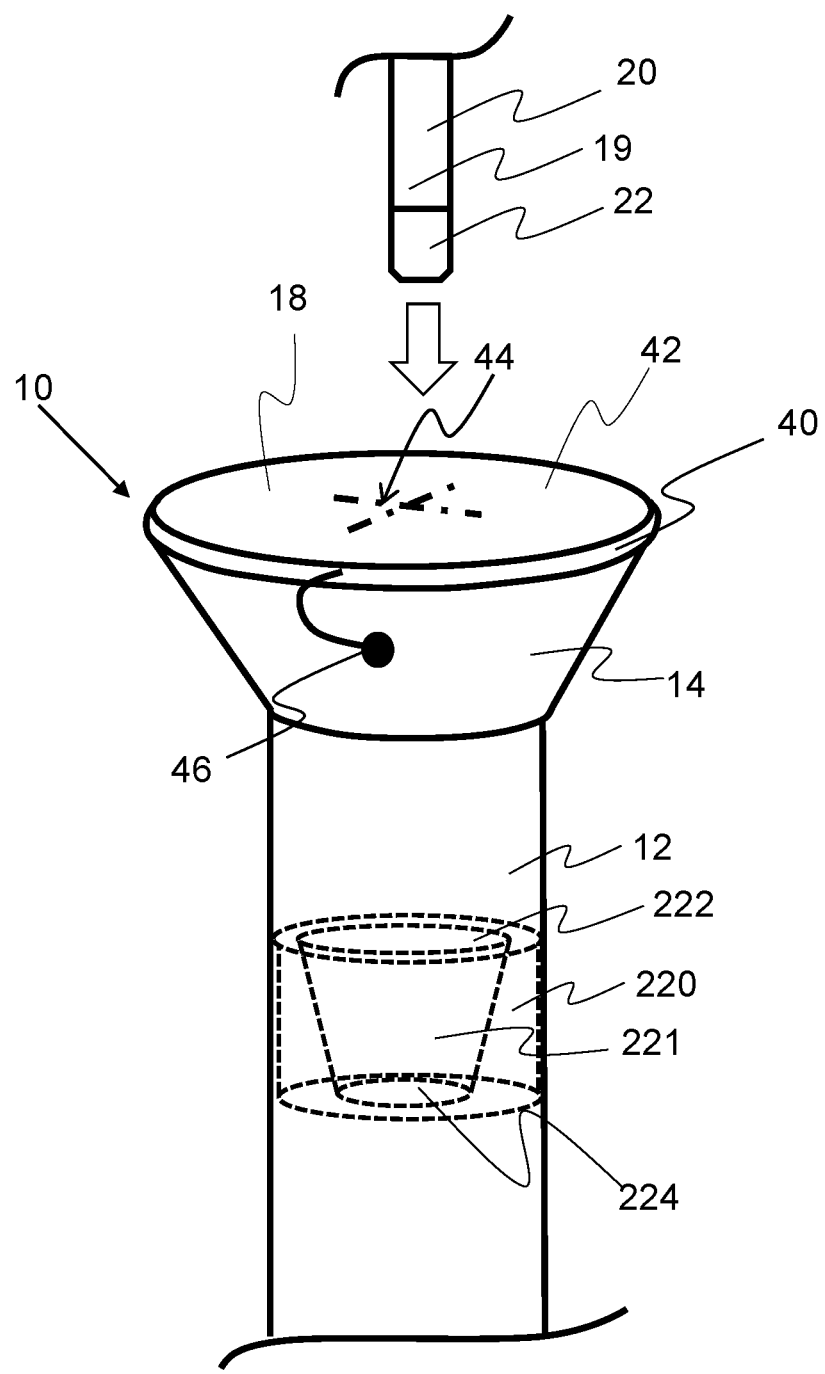
FIG. 3A shows an isometric view of the second end of a multifunctional enclosure described herein having a second end cover.
Figure 3B:
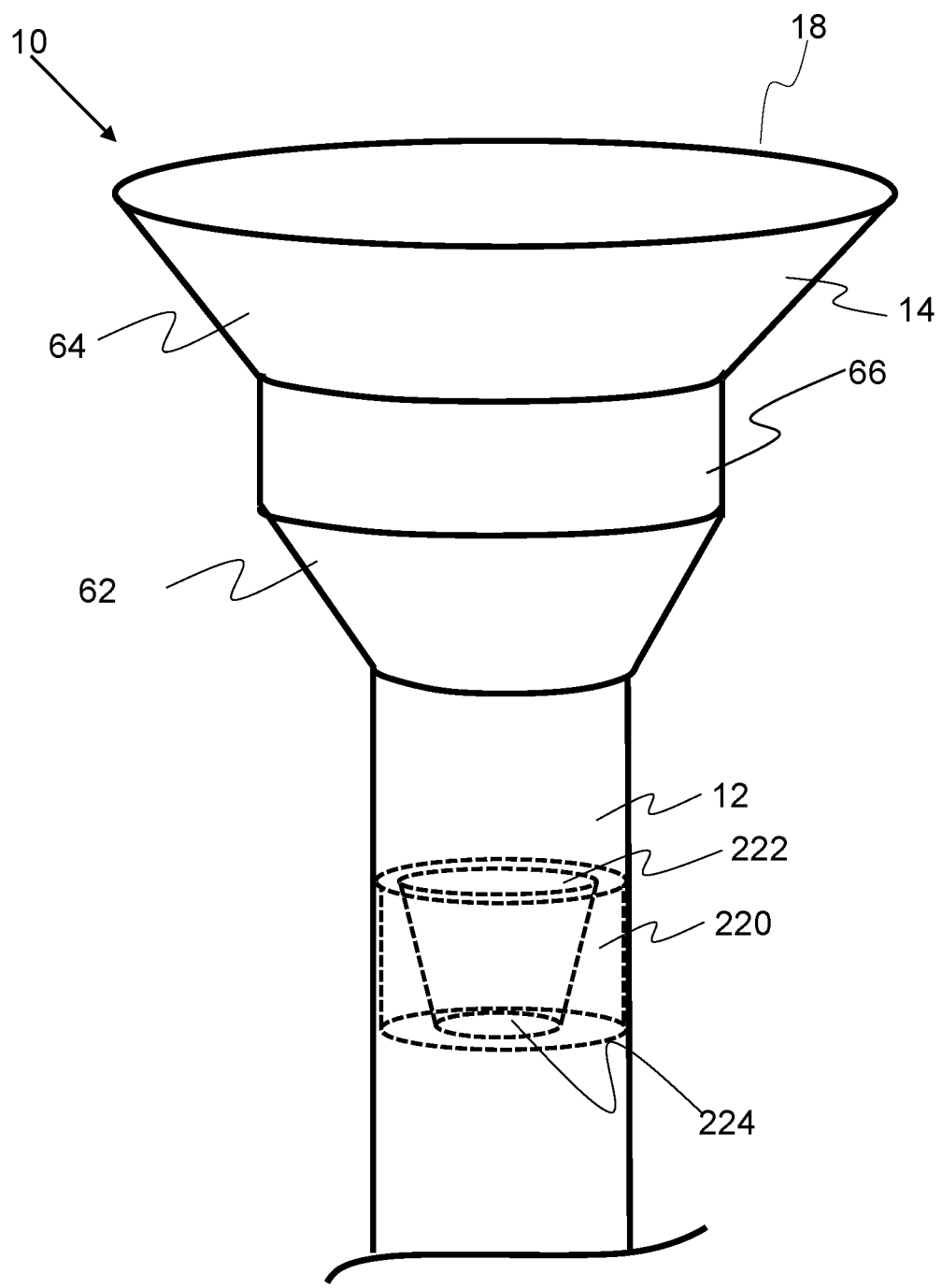
FIG. 3B shows an isometric view of the second end of a multifunctional enclosure described herein.

The second end 18 or opening of the multifunctional enclosure 10 may comprise an enlarged end 14, or configured to facilitate the insertion of the medical probe, as shown in FIG. 3A. The second end may be any suitable shape such as a funnel or bell shape. As shown in FIG. 3A the enlarged end 14 is in a funnel shape, where the second end 18 is larger in diameter than the elongated sleeve 12. As shown in FIG. 3B, the enlarged end 14 comprises a plurality of shapes, including a first funnel shape portion 62 and a second funnel shape portion 64. A straight shape portion 66 connects the two funnel shape portions as shown in FIG. 3B.

Figure 3C:
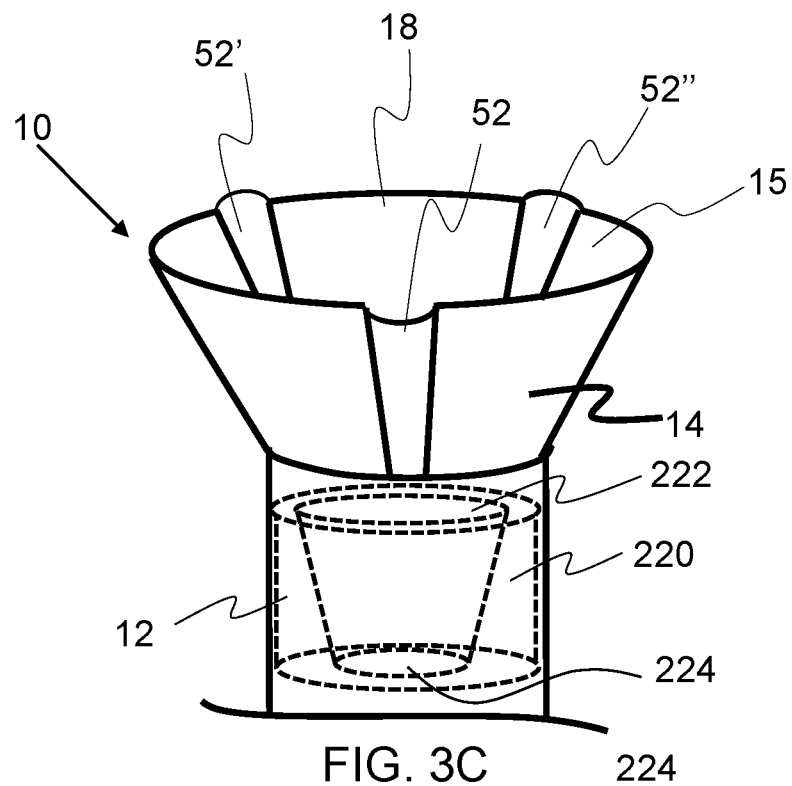
FIG. 3C shows an isometric view of the second end of a multifunctional enclosure described herein having flutes.
Figure 3D:
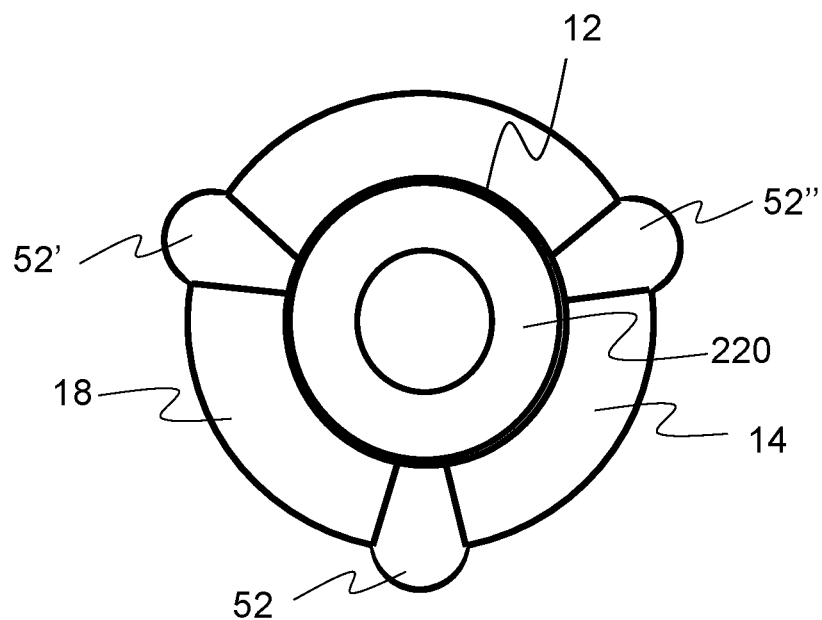
FIG. 3D shows a top down view of the second end of a multifunctional enclosure described herein having flutes.

The enlarged portion 14 may further comprise flutes 52, 52' and 52" as shown in FIGS. 3C and 3D. The flutes may be configured into the enlarged portion to allow the passage of air when a medical probe is inserted into the multifunctional enclosure. In some embodiments, the medical probe may fit snugly into the opening 15 at the second end 18 of the multifunctional enclosure and effectively prevent air passage through the second end into the elongated sleeve. The flutes may have any suitable shape such as a curved or angled shape. The flutes may extend the entire length of the enlarged portion, or only a portion of the length of the enlarged portion. In one embodiment, a flute or flutes may extend along a portion of the elongated sleeve.

In one embodiment, the second end comprises a cover 40 that may be removed to allow for the insertion of the medical probe. In an alternative embodiment, the second end cover 40 may comprise an opening 44, such as a hole or at least one slit, whereby the medical probe 20 may be inserted, as shown in FIG. 3A. The second end cover may protect the interior of the multifunctional enclosure from contamination prior to use. In one embodiment, the multifunctional enclosure comprises two second end covers; one being solid, and the other having an opening. In this embodiment, the solid second end cover may be removed and the medical probe may be inserted through the opening in the second end cover. The second end cover may also be attached to the multifunctional enclosure by a second end cover attachment portion 46, as shown in FIG. 3A.

The attachment component 50, as shown in FIG. 1 may comprise any number of components configured to attach the multifunctional enclosure 10 to the medical probe 20. The attachment component may include for example, elastic bands, hooks, latches, hook and loop fasteners and the like. In one embodiment, the attachment component comprises at least one elastic band that may be detachably attached to the medical probe, such as by stretching the band and locating the stretched end over a portion or projection of the medical probe.

Figure 7:
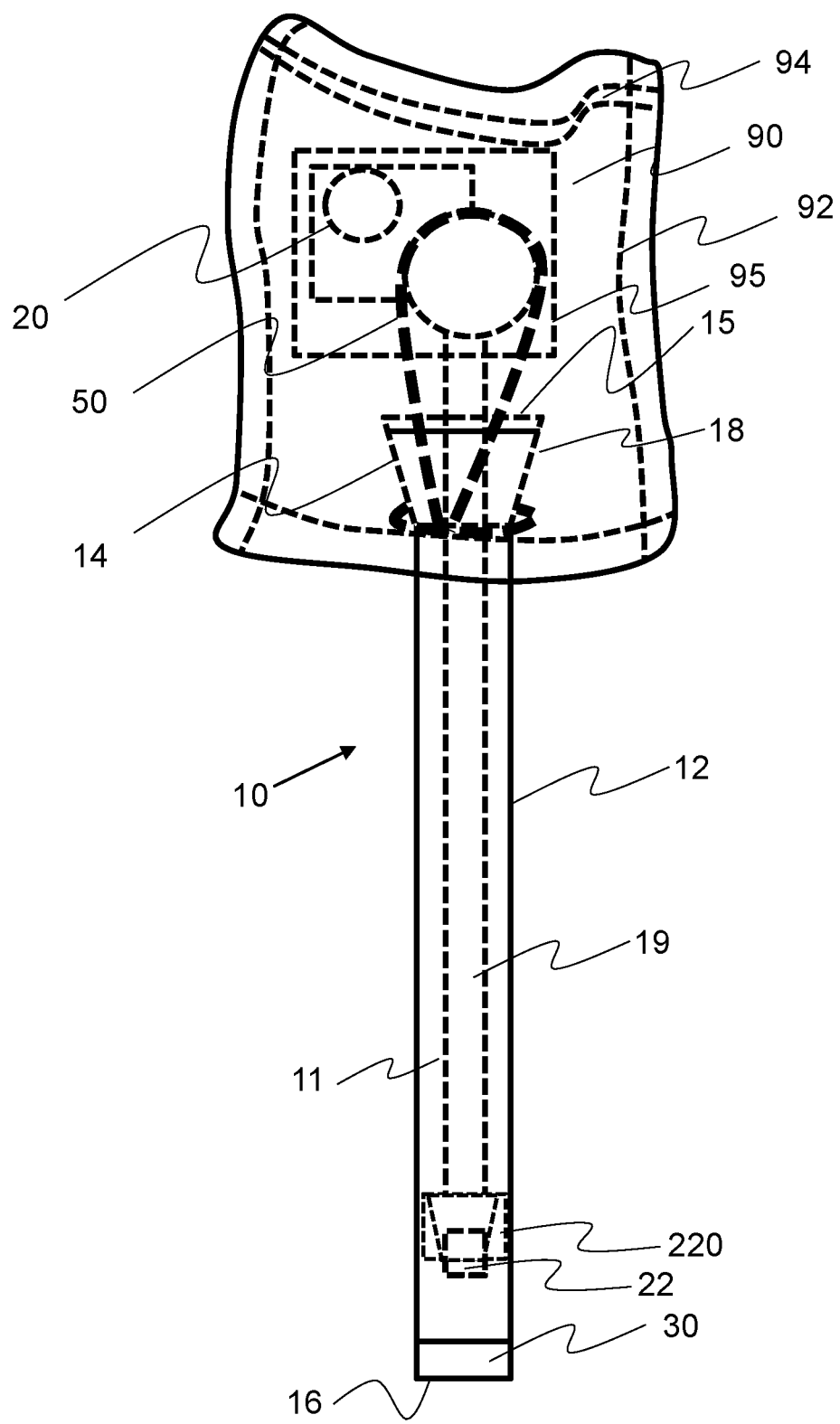
FIG. 7 shows a side view of a multifunctional enclosure described herein having an enclosure pouch.

FIG. 7 illustrates the multifunction enclosure according to one embodiment of the present invention. It depicts a medical probe 20 for use with the multifunction enclosure 10. The medical probe 20 includes a handle portion 95 and an elongated portion 19. The multifunctional enclosure 10 may further comprise an enclosure pouch 90 that may be configured to enclose the medical probe 20 as shown in FIG. 7. In one embodiment, the enclosure pouch 90 is attached to the multifunctional enclosure 10 and comprises a sealing portion 94 along the extended end that may be used to seal the medical probe 20 within the enclosure pouch as shown in FIG. 7. The elongated portion 19 of the medical probe 20 is inserted through the opening 15 in the second end 18 of the multifunction enclosure 10, and is further restrained by the attachment component 50 that is looped around a portion of the medical probe as shown in FIG. 7. The pouch may comprise any suitable material including but not limited to plastic, metal foil, fabric, antimicrobial materials, such as porous or microporous materials, combinations of material, and the like. The pouch 90 may be a sterilization pouch, and may comprise a porous side and a non-porous side. For example, the pouch may comprise a paper side and a plastic side. The sealing portion of the pouch 94 may comprise any suitable sealing mechanism or material, including but not limited to a zipper, hook and loop fastener, adhesive, interference fit seal, thermally welded seal, and the like. Some special adhesive zones 94 can be configured to aid in sealing around cables and tubing that extend from some styles of endoscopes.

Figure 9:
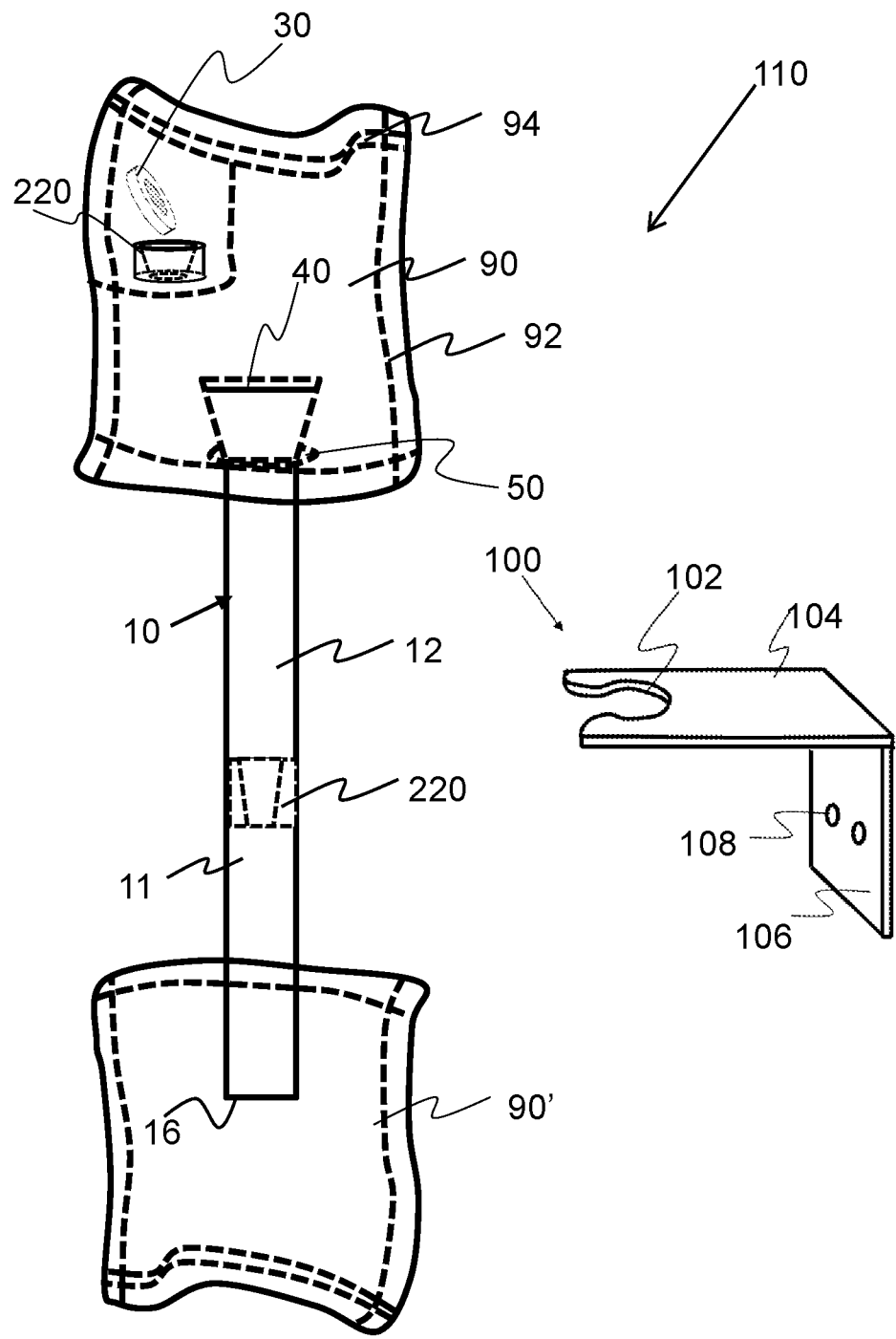
FIG. 9 shows an isometric view of a multifunctional enclosure kit described herein.

In one embodiment, both the first and second end of the multifunctional enclosure comprise a pouch 90 and 90' that may be removed prior to using the multifunctional enclosure as shown in FIG. 9. The pouches may be attached to one or both ends of the multifunctional enclosure to prevent contamination of the interior 11 of the multifunctional enclosure. The pouches may be attached to the multifunctional enclosure through any suitable means including but not limited to tape, adhesives, heat welding, ultrasonic welding and the like.

The multifunctional enclosure describe herein may be positioned and temporarily restrained by a bracket 100, as shown in FIGS. 8A, 8B and 8C. The bracket 100 as shown in FIG. 8A, may have an opening 102 configured in a first member to accept the multifunctional enclosure. The multifunctional enclosure may slide direct into the bracket and the enlarged end of the multifunctional enclosure may support the enclosure. A second member 106 may be attached to the first member 104 of the bracket as shown in FIG. 8A. In addition, the bracket may further comprise at least one attachment portion, such as a hole or holes 108 as shown in FIG. 8A. The opening 102 in the bracket 100 may be configured in any suitable manner to accept and support the multifunctional enclosure as described herein.

As shown in FIG. 8D, the multifunctional enclosure describe herein may be positioned within an opening 102 of a first member 104, which may include a plurality of openings for retaining a plurality of multifunctional enclosures. A handle 204, may be coupled with the first member to enable a person to carry a plurality of multifunctional enclosures.

The multifunction enclosure as described herein may be provided as a kit 110 as shown in FIG. 9. The kit 110 may include at least one multifunctional enclosure 10, and a bracket 100. The kit may further include at least one pouch 90 attached to at least one end of the multifunctional enclosure, an attachment component 50, a first end closure portion 30, and a second end cover 40. The first end closure portion 30 may be attached to the first end, or it may be within one of the pouches 90 as shown in FIG. 9.

As shown throughout the figures, a probe retainer 220 is configured to extend around the elongated portion 19 or the medical device 22 of the medical probe 20. The medical device 22 on the extended end 24 of the elongated portion 19 may be fragile and preventing it from jostling within the elongated sleeve 12 may be important to prevent damage to the medical device 22. An exemplary probe retainer 220 fits within the elongated sleeve 12 and has an aperture 221 extending from a proximal opening 222. The aperture 221 may be a through aperture and extend from the proximal opening to a distal opening 224. The proximal opening 222 may be larger in dimension or diameter than the distal opening 224 and may be configured proximal to the second end 18 or the opening 15 of the elongated member for insertion of the elongated portion 19. The aperture 221 may taper in dimension from the proximal opening 222 toward the distal opening. The probe retainer 220 may be configured within the elongated member 12 and may be configured to slide with the elongated member down toward the first end 16 upon insertion of the elongated portion 19 of the medical probe 20. In this way, medical probes with various length elongated members may have the medical device on the extended end protected as the probe retainer slides down with the elongated member to be positioned proximal to the medical device. The distal opening may be smaller than a diameter of the elongated portion 19, or the medical device 22 and may stay configured around the extended end of the elongated member.

As shown in FIG. 1, a probe retainer 220 may be inserted into the elongated sleeve 12 prior to insertion of the elongated portion 19. As shown in FIGS. 2A, 2B, 2C, and 2D, the probe retainer may be configured proximal to the first end 16 wherein the extended end of the elongated member rests within the aperture 221 of the probe retainer. As shown in FIGS. 3A, 3B, 3C and 3D, the probe retainer 220 is configured proximal to the second end 18, or the opening 15 in the second end 18 of the multifunction enclosure 10, wherein the probe retainer may slide down with the elongated member upon insertion of the elongated member, as shown in FIG. 4 and as indicated by the bold arrows. As shown in FIG. 7, the probe retainer 220 has slid down with the medical device 22 of the medical probe 20. As shown in FIG. 9, the probe retainer 220 may be configured within the enclosure pouch 90. A user may remove the probe retainer 220 and insert it into the elongated sleeve 12 or over the extended end of the elongated portion 19 of the medical probe 22.

The multifunctional enclosure as described herein may be used in a variety of ways. In one method of use, a medical probe or the elongated member of a medical probe may be inserted into the multifunctional enclosure as described herein, and the medical probe may be securely transported to and/or from, a medical procedural room, storage area, cleaning facility, repair facility, manufacturer, or a sterilization procedure. In another embodiment, the multifunctional enclosure may be used as a reservoir for fluids that may be coated onto the medical probe prior or after a procedure. For example, the medical probe may be coated with a sterilization fluid prior to a procedure by introducing the fluid into the multifunctional enclosure. The medical probe may then be removed from the multifunctional enclosure and inserted into a patient. The fluid may be simply poured into the second end of the multifunctional enclosure, or a filling port 24, may be configured on the multifunctional enclosure for accepting fluid, as shown in FIG. 4. The filling port may have an adjustable, one way, check valve, or a cover to prevent contaminates from entering the multifunctional enclosure. In addition, the medical probe may be coated or treated with a cleaning solution or sterilization fluid after a procedure. For example, a cleaning fluid such as enzyme soap, for example, may be introduced into the multifunctional enclosure, and the medical probe may be inserted into the multifunctional enclosure for post procedural cleaning. Quickly treating the medical probe with a cleaning or sterilization fluid after a procedure may reduce the risk of cross contamination occurring and may provide for more effective and complete removal of biological material.

The multifunctional enclosure as described herein may be disposable, or may be reusable. A first multifunctional enclosure may be used for sterilization and transport to a medical procedure, and a second multifunctional enclosure may be used for post treatment transport and cleaning.

EXAMPLE

A 30 in long polyethylene terephthalate (PETG) tube having an outer diameter of 0.848 in and a wall thickness of 0.022 in was flared at one end. The flared end, or second end, had a funnel shape and a second end diameter of 1.8 in, and the flared length was approximately 1 in, as measured along the length axis of device. A latex free, synthetic rubber elastic band approximately 3 in in diameter, 0.125 in wide, and 0.0625 in long was configured around the elongated sleeve. A sterilization enclosure pouch available from AMCOR Ltd., having a paper side and a plastic side was attached to the multifunctional enclosure, by a combination of heat sealing and double sided tape.

DEFINITIONS

Multifunctional enclosure as used herein is defined as an enclosure that is configured to cover at least the elongated portion of a medical probe and is not configured for insertion into the body.

Medical probe as used herein is defined as any medical device that is inserted into the body for the purpose of imaging, diagnosis and treatment, including but not limited to endoscope, catheter, pressure transducer or ultrasonic imaging device. A medical probe may comprise a flexible or rigid elongated member.

Rigid as used herein in reference to the elongated sleeve portion of the multifunctional enclosure, means that the elongated sleeve will prevent the elongated member of the medical probe from swinging or moving freely. The elongated sleeve may have some flexible properties, such as a plastic tube that may bend to a certain degree under a load, but will permanently deform if bent too far.

Detachably attached as used herein in reference to the first end closure portion means that the first end closure portion can be temporarily attached to the first end of the multifunctional enclosure, such as by screwing, pushing, or snapping on, for example.

As used herein "closure portion," "cover," and "cover portion" are used synonymously to convey a structure that may "close" an opening to limit ingress and egress of fluids or gases to varying degrees.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A multifunctional enclosure system for covering an elongated portion of a medical probe, comprising:
   a) an elongated rigid sleeve comprising:
      i) an interior configured to receive said medical probe;
      ii) a first end;
      iii) a second end comprising an opening, wherein said second end opening is configured for the insertion of said elongated portion of a medical probe; and
      iv) a length extending between said first end and said second end;
   b) a first end closure portion configured on said first end;
   c) a second end cover configured over the second end opening, wherein said interior of said elongated rigid member is protected from contamination prior to use by said second end cover over said second end opening and by said first end closure portion on said first end; and
   d) an attachment component configured to restrain said medical probe to said multifunctional enclosure with said elongated portion of said medical probe configured within said elongated sleeve, and configured to detachably attach to the medical probe;
   e) a probe retainer comprising an aperture and configured to extend between the elongated portion of the medical probe and the interior of the elongated rigid sleeve;
   wherein said attachment component comprises an elastomeric band configured to attach to the medical probe by stretching over a portion of said medical probe from said multifunctional enclosure.

2. The multifunctional enclosure system of claim 1, wherein the probe retainer extends completely around the elongated portion of the medical probe.

3. The multifunctional enclosure system of claim 1, wherein the aperture of the probe retainer is a through aperture extending from a proximal opening to a distal opening.

4. The multifunctional enclosure system of claim 1, wherein the probe retainer is elastic.

5. The multifunctional enclosure system of claim 2, wherein the probe retainer comprises foam.

6. The multifunctional enclosure system of claim 5, wherein the probe retainer is configured in the elongated rigid sleeve proximal to the second end and wherein the probe retainer is configured to slide along the elongated rigid sleeve with the elongated portion of the medical probe when it is inserted into the elongated rigid sleeve.

7. The multifunctional enclosure system of claim 1, wherein the probe retainer is configured in the elongated rigid sleeve proximal to the second end and wherein the probe retainer is configured to slide along the elongated rigid sleeve with the elongated portion of the medical probe when it is inserted into the elongated rigid sleeve.

8. The multifunctional enclosure system of claim 1, further comprising a removable pouch configured over the second end of the elongated rigid sleeve.

9. The multifunctional enclosure system of claim 8, wherein the probe retainer is configured in the removable pouch and configured to be inserted around the elongated portion of the medical probe prior to insertion of the elongated portion into the elongated rigid sleeve.

10. The multifunctional enclosure system of claim 8, wherein the removable pouch is sealed over the second end opening to prevent contamination of the elongated sleeve prior to insertion of the sterilized medical probe into the elongated sleeve.

11. The multifunctional enclosure system of claim 1, wherein the first end closure is a seam of the elongated rigid sleeve.

12. The multifunctional enclosure system of claim 1, wherein the first end closure is a molded end of the elongated rigid sleeve.

13. The multifunctional enclosure system of claim 1, further comprising a bracket having a plurality of openings for receiving a plurality of elongated rigid sleeves.

14. A method of containing a medical probe comprising:
   providing the multifunctional enclosure system of claim 1;
   removing the second end cover;
   inserting the elongated portion of said medical probe into the elongated rigid sleeve;
   wherein the elongated portion of the medical probe extends into the elongated rigid sleeve through said opening at the second end of the elongated rigid sleeve;
   wherein the elongated portion of the medical probe is contained within the elongated rigid sleeve;
   attaching the attachment component to the medical probe to retain the medical probe with the elongated portion of the medical probe configured within the elongated rigid sleeve;

transporting said medical probe with the elongated portion of the medical probe in the elongated rigid sleeve;
wherein the elongated portion of the medical probe is prevented from swinging or moving freely during transporting by the elongated rigid sleeve.

15. The method of claim 14,
further providing a removable pouch configured over the opening of the second end of the elongated rigid sleeve;
wherein the removable pouch is sealed over the second end opening to prevent contamination of the elongated sleeve prior to insertion of the sterilized medical probe into the elongated sleeve
removing the removable pouch from the enclosure to expose an opening in the second end;
inserting the elongated portion of a medical probe into the elongated sleeve of the rigid disposable plastic multifunctional enclosure;
wherein the elongated portion of the medical probe extends into the enclosure through said opening at the second end of the enclosure;
wherein the elongated portion of the probe is contained within the elongated sleeve of the enclosure;
attaching the attachment component to the medical probe to retain the medical probe with the elongated portion of the medical probe configured within the elongated rigid sleeve;
transporting said medical probe with the elongated portion of the medical probe in the elongated rigid sleeve; and
wherein the elongated portion of the medical probe is prevented from swinging or moving freely during transport by the elongated rigid sleeve.

16. The method of claim 15, wherein the probe retainer is configured in the removable pouch, and wherein the method further includes removing the probe retainer from the removable pouch and configuring the probe retainer between the elongated portion of the medical probe and the interior of the elongated rigid sleeve.

17. The method of claim 15, wherein the probe retainer is placed over the elongated portion of the medical probe prior to insertion of said elongated portion into the elongated rigid sleeve.

18. The method of claim 15, further providing a cap configured over the opening of the second end of the elongated rigid sleeve; and further removing the cap prior to insertion of the elongated portion of the medical probe into the elongated rigid sleeve.

* * * * *